United States Patent
Riordan

(10) Patent No.: US 10,172,898 B2
(45) Date of Patent: Jan. 8, 2019

(54) STEM CELL/ENDOTHELIAL PROGENITOR CELL MOBILIZATION BY NUTRACEUTICAL FORMULATIONS

(76) Inventor: Neil H. Riordan, Chandler, AZ (US)

( * ) Notice: Subject to any disclaimer, the term of this patent is extended or adjusted under 35 U.S.C. 154(b) by 1597 days.

(21) Appl. No.: 12/963,631

(22) Filed: Dec. 9, 2010

(65) Prior Publication Data
US 2011/0135759 A1 Jun. 9, 2011

Related U.S. Application Data

(60) Provisional application No. 61/285,171, filed on Dec. 9, 2009.

(51) Int. Cl.
| | |
|---|---|
| *A61K 36/481* | (2006.01) |
| *A61K 31/366* | (2006.01) |
| *A61K 31/593* | (2006.01) |
| *A61K 31/716* | (2006.01) |
| *A61K 36/815* | (2006.01) |
| *A61K 36/82* | (2006.01) |

(52) U.S. Cl.
CPC .......... *A61K 36/481* (2013.01); *A61K 31/366* (2013.01); *A61K 31/593* (2013.01); *A61K 31/716* (2013.01); *A61K 36/815* (2013.01); *A61K 36/82* (2013.01)

(58) Field of Classification Search
None
See application file for complete search history.

(56) References Cited

U.S. PATENT DOCUMENTS

2006/0182724 A1* 8/2006 Riordan ................. A61K 8/982
424/93.7

* cited by examiner

*Primary Examiner* — Terry A McKelvey
*Assistant Examiner* — Catheryne Chen
(74) *Attorney, Agent, or Firm* — Baumgartner Patent Law; Marc Baumgartner

(57) ABSTRACT

Compositions of matter, uses, and formulations of food supplements/nutrients capable of eliciting mobilization of various stem/progenitor cells, including hematopoietic stem cells and endothelial progenitor cells are disclosed. In one embodiment a formulation contains a mixture of ellagic acid, vitamin D3, beta 1,3 glucan and a ferment of the bacterium, *Lactobacillus fermentum*, with an extract of green tea, extract of goji berries, and extract of the root of *astragalus* added prior to fermentation. Said formulation, originally developed as an antioxidant/immune stimulator was found to have the unexpected property of eliciting stem/progenitor cell mobilization.

1 Claim, 7 Drawing Sheets

CHU-Hill colonies of EPCs stained by Giemsa stain.

Images of the cells grown in wells with growth factors (a) and without growth factors (b) (magnification x200).

Halo assay

STEM CELL/ENDOTHELIAL PROGENITOR CELL MOBILIZATION BY NUTRACEUTICAL FORMULATIONS

CROSS-REFERENCE TO RELATED APPLICATIONS

This application claims priority to Provisional Application Ser. No. 61/285,171 filed on Dec. 9, 2009, which is expressly incorporated by reference in its entirety

FIELD OF THE INVENTION

The invention pertains to the area of nutraceutical products. More specifically, the invention provides novel compositions useful for properties of altering stem/progenitor cell distribution. Furthermore, the invention relates to means of eliciting therapeutic effects through mobilization of stem/progenitor cells from compartments of the body.

BACKGROUND

Stem cell therapy can broadly be divided into approaches aimed at de novo regeneration of injured organs, or into the use of the stem cells to accelerate endogenous healing processes. It appears that adult stem cells are stored in reservoirs ready to meet the body's need subsequent to injury. For example, in conditions as diverse as renal injury [1], myocardial infarct [2], stroke [3], irradiation [4], and acoustic damage [5], injured tissue has been reported to cause upregulation of the chemokine stromal derived factor (SDF)-1, which causes mobilization and attraction of bone marrow derived stem/progenitor cells.

Augmentation or de novo initiation of the mobilization process has been performed therapeutically using cytokines such as G-CSF [6], GM-CSF [7], and Parathyroid Hormone [8]. Recently small molecule antagonists of CXCR4 have entered clinical use [9]. Therapeutic benefits of mobilization have been seen in models of: a) radiation induced salivary gland damage [10, 11]; b) cardiac infarct [12]; c) stroke [13]. Clinically, mobilization therapy has been attempted in conditions such as ALS [14], heart failure [15, 16], and liver failure [17].

Unfortunately, agents used in the mobilization of stem cells/EPC such as G-CSF, GM-CSF, and Parathyroid Hormone are expensive and can not be continually administered for long periods of time. Thus there is a need for agents which induce augmentation of circulating stem cell/EPC levels that can be administered chronically, without adverse effects, and is relatively inexpensive. Jensen et al reported an extract from the edible cyanobacterium Aphanizomenon flos-aquae (AFA) enriched for a novel ligand for human CD62L (L-selectin), which is currently sold commercially under the name StemEnhance [18]. Although this compound is relatively innocuous from a toxicity perspective, mobilization appears to be mediated in a non-specific manner. In healthy volunteers a transient, 18% increase in numbers of circulating CD34+ stem cells was noted that maximized 1 hour after consumption. Given this relatively insignificant increase and transient nature of mobilization, as well as the fact that mechanistically mobilization is associated with decrease in CXCR4, which would block homing of stem cells to target tissue, novel methods of mobilization stem/progenitor cells are needed that are useful for long-term administration.

SUMMARY OF THE INVENTION

Teachings herein are directed to compositions comprising ellagic acid, vitamin D3, beta 1,3 glucan and a ferment of the bacterium, *Lactobacillus fermentum*, with an extract of green tea, extract of goji berries, and extract of the root of *astragalus* added prior to fermentation.

Additionally the teachings herein are directed to methods of mobilizing endothelia progenitor cells comprising administration of a sufficient dose of a composition comprised of ellagic acid, vitamin D3, beta 1,3 glucan and a ferment of the bacterium, *Lactobacillus fermentum*, with an extract of green tea, extract of goji berries, and extract of the root of *astragalus* added prior to fermentation.

Further embodiments are directed to: a method of mobilizing endothelia progenitor cells comprising administration of a sufficient dose of a composition comprised of ellagic acid, vitamin D3, beta 1,3 glucan and a ferment of the bacterium, *Lactobacillus fermentum*, with an extract of green tea, extract of goji berries, and extract of the root of *astragalus* added prior to fermentation. The endothelial progenitor cells can be positive for expression of KDR and CD34. The endothelial progenitor cells can also be capable of forming endothelial cells in tissue culture.

Further embodiments are directed to methods of decreasing oxidative stress in a patient comprising administration of a sufficient dose of a composition comprised of ellagic acid, vitamin D3, beta 1,3 glucan and a ferment of the bacterium, *Lactobacillus fermentum*, with an extract of green tea, extract of goji berries, and extract of the root of *astragalus* added prior to fermentation. The composition can be formulated as a neutraceutical, dietary supplement or wholistic formulation for oral administration.

Further embodiments are directed to methods of treating a disorder associated with reduced levels of circulating stem/progenitor cells by administration of a sufficient concentration of a sufficient dose of a composition comprised of ellagic acid, vitamin D3, beta 1,3 glucan and a ferment of the bacterium, *Lactobacillus fermentum*, with an extract of green tea, extract of goji berries, and extract of the root of *astragalus* added prior to fermentation.

Additional methods can involve increasing endothelial health, as assessed by the flow mediated dilation assay, comprising administration of a sufficient dose of a composition comprised of ellagic acid, vitamin D3, beta 1,3 glucan and a ferment of the bacterium, *Lactobacillus fermentum*, with an extract of green tea, extract of goji berries, and extract of the root of *astragalus* added prior to fermentation.

Still further embodiments include methods of preventing a degenerative condition in a mammal through the steps of: a) identifying a deficiency in numbers and/or activity of circulating endothelial progenitor cells; b) administering a nutritional supplement capable of augmenting circulating levels of endothelial progenitor cells based on deficiency identified; c) re-assessing circulating endothelial progenitor cell numbers; and d) further adjusting dose of said nutritional supplement based on response to supplementation.

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE ILLUSTRATED EMBODIMENTS

Figure 1:
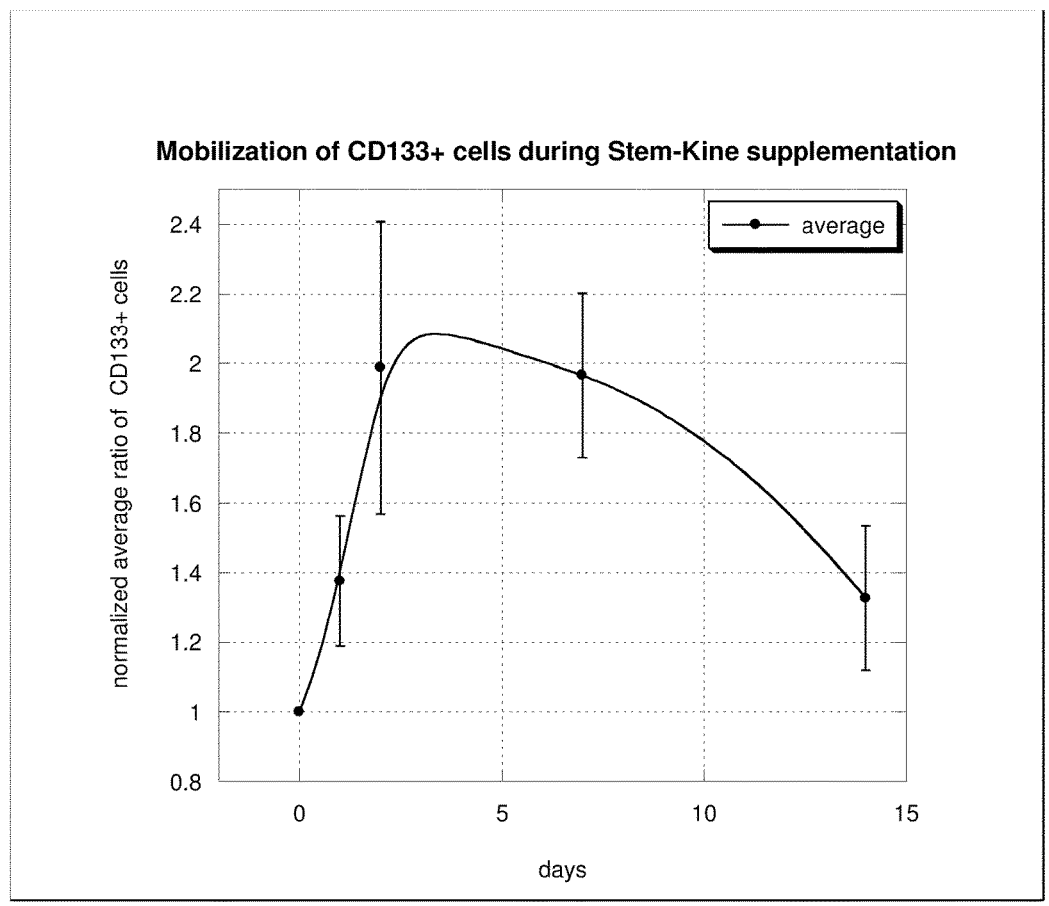
FIG. 1 is a graph depicting the mobilization of CD133+ cells during Stem-Kine supplementation.

Embodiments of the present invention are described below. It is, however, expressly noted that the present invention is not limited to these embodiments, but rather the intention is that modifications that are apparent to the person skilled in the art and equivalents thereof are also included.

A formulation of ellagic acid; vitamin D3; beta 1,3 glucan; a ferment of the bacterium, *Lactobacillus fermentum* was prepared which was mixed with green tea extract, extract of goji berries, and extract of the root of *astragalus*, and subsequently fermented with *Lactobacillus fermentum* in a manner similar to that used for production of the food supplement 1 mm-Kine, as described in part in U.S. Pat. No. 6,827,940. The formulation was developed as a nutritional supplement useful for immune stimulation and anti-oxidant activity.

Rationale for antioxidant activity was based on the known properties of the individual ingredient. Specifically, ellagic acid is a polyphenol antioxidant found in numerous vegetables and fruits; vitamin D3 has antioxidant and immune stimulating activities; beta 1,3 glucan stimulates macrophages and hence is immune modulatory. Green tea extracts and some components of goji berries are known to possess antioxidant characteristics. Additionally, astragalosides and other molecules found in the root of *astragalus* are known antioxidants that can prevent cellular damage secondary to oxidation.

In testing the product in healthy volunteers, benefit in various health conditions was observed. Specifically, increased level of energy, improvement of skin conditions around fingernails, better sleep, and increased mental acuity was reported. These properties prompted us to test effects of the composition on stem cell and endothelial progenitor cell (EPC) mobilization. The data generated produced the unexpected finding of a profound mobilization effect associated with intake of this food supplement.

The current invention teaches methods of inducing mobilization of stem cells using various compounds currently found in the food supply. Through this "nutraceutical" approach, stem cell mobilization may be produced using inexpensive means that are substantially free of adverse effects that are associated with currently used approaches for stem cell mobilization.

In one embodiment the invention comprises a composition of ellagic acid, vitamin D3, beta 1,3 glucan and a ferment of the bacterium, *Lactobacillus fermentum*, with an extract of green tea, extract of goji berries, and extract of the root of *astragalus* added prior to fermentation. Said composition is capable of augment number of hematopoietic and endothelial progenitor cells in circulation.

In one embodiment, the invention provides means of maintaining endothelial health through administration of a composition of ellagic acid, vitamin D3, beta 1,3 glucan and a ferment of the bacterium, *Lactobacillus fermentum*, with an extract of green tea, extract of goji berries, and extract of the root of *astragalus* added prior to fermentation. The endothelium plays several functions essential for life, including: a) acting as an anticoagulated barrier between the blood stream and interior of the blood vessels; b) allowing for selective transmigration of cells into and out of the blood stream; c) regulating blood flow through controlling smooth muscle contraction/relaxation; and d) participating in tissue remodeling [19]. A key hallmark of the aging process and perhaps one of the causative factors of health decline associated with aging appears to be loss of endothelial function. Whether as a result of oxidative stress, inflammatory stress, or senescence, deficiencies in the ability of the endothelium to respond to physiological cues can alter the ability to think [20], procreate [21], see [22], and breathe [23]. Specifically, minute alterations in the ability of endothelium to respond to neurotransmitter induced nitric oxide causes profound inability to perform even simple mental functions [24, 25]. Small increases in angiogenesis in the retina as a result of injury or glucose are associated with wet macular degeneration blindness [26]. Atherosclerosis of the penile vasculature is a major cause of erectile dysfunction [27]. The pulmonary endothelium's sensitivity to insult can cause hypertension and associated progression to decreased oxygen delivery [28].

Health of the endothelium can be quantified using several methods, including assessment of the physical and mechanical features of the vessel wall, assaying for production of systemic biomarkers released by the endothelium, and quantification of ability of blood vessels to dilate in response to increased flow [29]. Of these, one of the most commonly used assays for endothelium function is the flow mediated dilation (FMD) assay. This procedure usually involves high resolution ultrasound assessment of the diameter of the superficial femoral and brachial arteries in response to reactive hyperemia induced by a cuff. The extent of dilatation response induced by the restoration of flow is compared to dilatation induced by sublingual glyceryl trinitrate. Since the dilatation induced by flow is dependent on the endothelium acting as a mechanotransducer and the dilatation induced by glyceryl trinitrate is based on smooth muscle responses, the difference in dilatation response serves as a means of quantifying one aspect of endothelial health [30, 31]. This assay has been used to show endothelial dysfunction in conditions such as healthy aging [32-34], as well as various diverse inflammatory states including renal failure [35], rheumatoid arthritis [36], Crohn's Disease [37], diabetes [38], heart failure [39], and Alzheimer's [40]. Although it is not clear whether reduction in FMD score is causative or an effect of other properties of endothelial dysfunction, it has been associated with: a) increased tendency towards thrombosis, in part by increased vWF levels [41], b) abnormal responses to injury, such as neointimal proliferation and subsequent atherosclerosis [42], and c) increased proclivity towards inflammation by basal upregulation of leukocyte adhesion molecules [43]. In one embodiment of the invention, endothelial health is quantified based on methods described above and known in the art. Knowledge of endothelial health is used to adjust dosage of administration for the composition of ellagic acid, vitamin D3, beta 1,3 glucan and a ferment of the bacterium, *Lactobacillus fermentum*, with an extract of green tea, extract of goji berries, and extract of the root of *astragalus* added prior to fermentation.

As part of age and disease associated endothelial dysfunction is the reduced ability of the host to generate new blood vessel [44]. This is believed to be due, at least in part, to reduction of ischemia inducible elements such as the HIF-1 alpha transcription factor which through induction of SDF-1 and VEGF secretion play a critical role in ability of endothelium to migrate and form new capillaries in ischemic tissues [45, 46]. Accordingly, if one were to understand the causes of endothelial dysfunction and develop methods of inhibiting these causes or stimulating regeneration of the endothelium, then progression of many diseases, as well as possible increase in healthy longevity may be achieved. Accordingly, in one embodiment, the composition of ellagic acid, vitamin D3, beta 1,3 glucan and a ferment of the bacterium, *Lactobacillus fermentum*, with an extract of green tea, extract of goji berries, and extract of the root of *astragalus* added prior to fermentation, is provided to decrease changes associated with endothelial aging. Concentration of the composition may be modified based on biological markers or endpoints associated with aging. These include ability of circulating EPC to migrate towards chemotactic gradients such as SDF-1, or hypoxia-responsiveness of HIF-1.

During development endothelial cells are believed to originate from a precursor cell, the hemangioblast, which is capable of giving rise to both hematopoietic and endothelial cells [47]. Classically the endothelium was viewed as a fixed structure with relatively little self renewal, however in the last two decades this concept has fundamentally been altered. The current hypothesis is that the endothelium is constantly undergoing self renewal, especially in response to stress. A key component of endothelial turnover appears to be the existence of circulating endothelial progenitor (EPC) cells that appear to be involved in repair and angiogenesis of ischemic tissues. An early study in 1963 hinted at the existence of such circulating EPC after observations of endothelial-like cells, that were non-thrombogenic and morphologically appeared similar to endothelium, were observed covering a Dacron graft that was tethered to the thoracic artery of a pig [48]. The molecular characterization of the EPC is usually credited to a 1997 paper by Asahara et al. in which human bone marrow derived VEGR-2 positive, CD34 positive monocyte-like cells were described as having ability to differentiate into endothelial cells in vitro and in vivo based on expression of CD31, eNOS, and E-selectin [49]. These studies were expanded into hindlimb ischemia in mouse and rabbit models in which increased circulation of EPC in response to ischemic insult was observed [50]. Furthermore, these studies demonstrated that cytokine-induced augmentation of EPC mobilization elicited a therapeutic angiogenic response. Using irradiated chimeric systems, it was demonstrated that ischemia-mobilized EPC derive from the bone marrow, and that these cells participate both in sprouting of pre-existing blood vessels as well as the initiation of de novo blood vessel production [51]. Subsequent to the initial phenotypic characterization by Asahara et al [49], more detailed descriptions of the human EPC were reported. For example, CD34 cells expressing the markers VEGF-receptor 2, CD133, and CXCR-4 receptor, with migrational ability to VEGF and SDF-1 has been a more refined EPC definition [52]. However there is still some controversy as to the precise phenotype of the EPC, since the term implies only ability to differentiate into endothelium. For example, both CD34+, VEGFR2+, CD133+, as well as CD34+, VEGFR2+, CD133− have been reported to act as EPC [53]. More recent studies suggest that the subpopulation lacking CD133 and CD45 are precursor EPC [54]. Other phenotypes have been ascribed to cells with EPC activity, one study demonstrated monocyte-like cells that expressing CD14, Mac-1 and the dendritic cell marker CD11c have EPC activity based on uptake of acetylated LDL and binding to the ulex-lectin [55, 56].

While the initial investigations into the biology of EPC focused around acute ischemia, it appears that in chronic conditions circulating EPC may play a role in endothelial turnover. Apolipoprotein E knockout (ApoE KO) mice are genetically predisposed to development of atherosclerosis due to inability to impaired catabolism of triglyceride-rich lipoproteins. When these mice are lethally irradiated and reconstituted with labeled bone marrow stem cells, it was found that areas of the vasculature with high endothelial turnover, which were the areas of elevated levels of sheer stress, had incorporated the majority of new endothelial cells derived from the bone marrow EPC [57]. The possibility that endogenous bone marrow derived EPC possess such a regenerative function was also tested in a therapeutic setting. Atherosclerosis is believed to initiate from endothelial injury with a proliferative neointimal response that leads to formation of plaques. When bone marrow derived EPC are administered subsequent to wire injury, a substantial reduction in neointima formation was observed [58]. The argument can obviously made that wire injury of an artery does not resemble the physiological conditions associated with plaque development. To address this, Wassmann et al [59], used ApoE KO mice that were fed a high cholesterol diet and observed reduction in endothelial function as assessed by the flow mediated dilation assay. When EPC were administered from wild-type mice restoration of endothelial responsiveness was observed.

In the context of aging, Edelman's group performed a series of interesting experiments in which 3 month old syngeneic cardiac grafts were heterotopically implanted into 18 month old recipients. Loss of graft viability, associated with poor neovascularization, was observed subsequent to transplanting, as well as subsequent to administration of 18 month old bone marrow mononuclear cells. In contrast, when 3 month old bone marrow mononuclear cells were implanted, grafts survived. Antibody depletion experiments demonstrated bone marrow derived PDGF-BB was essential in integration of the young heart cells with the old recipient vasculature [60]. These experiments suggest that young EPC or EPC-like cells have ability to integrate and interact with older vasculature. What would be interesting is to determine whether EPC could be "revitalized" ex vivo by culture conditions or transfection with therapeutic genes such as PDGF-BB.

Accordingly, in one embodiment the invention teaches the use of the composition of ellagic acid, vitamin D3, beta 1,3 glucan and a ferment of the bacterium, *Lactobacillus fermentum*, with an extract of green tea, extract of goji berries, and extract of the root of *astragalus* added prior to fermentation, in the rejuvenation of blood vessels by modulation of the circulating EPC compartment.

Tissue injury and hypoxia are known to generate chemoattractants that potentially are responsible for mobilization of EPC. Reduction in oxygen tension occurs as a result of numerous injuries including stroke, infarction, or contusion. Oxygen tension is biologically detected by the transcription factor HIF-1 alpha, which upon derepression undergoes nuclear translocation. This event causes upregulated expression of a plethora of angiogenesis promoting cytokines and chemoattractants [61], such as stromal derived factor (SDF)-1 and VEGF [62, 63]. On the other hand, tissue necrosis causes release of "danger signals" such as HMBG1, a nuclear factor that has direct chemoattractant activity on mesoangioblasts, a type of EPC [64, 65]. It has been demonstrated that this systemic release of chemoattractant cytokines after vascular injury or infarct is associated with mobilization of endogenous bone marrow cells and EPC [66].

Myocardial infarction has been widely studied in the area of regenerative medicine in which cellular and molecular aspects of host response post-injury are relatively well defined. EPC mobilization after acute ischemia has been demonstrated in several cardiac infarct studies. This was first reported by Shintani et al who observed increased numbers of CD34 positive cells in 16 post infarct patients on day 7 as compared to controls. The rise in CD34 cells correlated with ability to differentiate into cells morphologically resembling endothelium and expressing endothelial markers KDR and CD31. Supporting the concept that response to injury stimulates EPC mobilization, a rise in systemic VEGF levels was correlated with increased EPC numbers [63]. A subsequent study demonstrated a similar rise in circulating EPC post infarct. Blood was drawn from 56 patients having a recent infarct (<12 hours), 39 patients with stable angina, and 20 healthy controls. Elevated levels of cells expressing CD34/CXCR4+ and CD34/CD117+ and c-met+ were observed only in the infarct patients which were highest at the first blood draw. In this study the mobilized cells not only expressed endothelial markers, but also myocytic and cardiac genes [67]. The increase in circulating EPC at early timepoints post infarction has been observed by other groups, and correlated with elevations in systemic VEGF and SDF-1 [68, 69].

In the case of cerebral infarction studies support the concept that not only are EPC mobilized in response to ischemia, but also that the extent of mobilization may be associated with recovery. In a trial of 48 patients suffering primary ischemic stroke, mobilization of EPC was observed in the first week in comparison to control patients. EPC were defined as cells capable of producing endothelial colony forming units. A correlation between improved outcome at 3 months and extend of EPC mobilization was observed based on the NIHSS and Rankin score [70]. In a similar study, Dunac et al reported on circulating CD34 levels of 25 patients with acute stroke for 14 days. A correlation between improvement on the Rankin scale and increased circulating CD34 cells was reported [71]. Noteworthy was that the level of CD34 mobilization was similar to that observed in patients treated with the mobilize G-CSF. In a larger study, Yip et al examined EPC levels in 138 consecutive patients with acute stroke and compared them to 20 healthy volunteers and in 40 at-risk control subjects [72]. Three EPC phenotypes were assessed by flow cytometry at 48 hours after stroke: a) CD31/CD34, b) CD62E/CD34, and c) KDR/CD34. Diminished levels of all three EPC subsets in circulation was predictive of severe neurological impairment NIHSS >/=12, while suppressed levels of circulating CD31/34 cells was correlated with combined major adverse clinical outcomes as defined by recurrent stroke, any cause of death, or NIHSS >/=12. Increased levels of the KDR/CD34 phenotype cells was strongly associated with NIHSS >or=4 on day 21. Although these studies do not directly demonstrate a therapeutic effect of the mobilized EPC, animal studies in the middle cerebral artery ligation stroke model have demonstrated positive effects subsequent to EPC administration [73, 74], an effect which appears to be at least partially dependent on VEGF production from the EPC [75].

Another ischemia-associated tissue insult is acute respiratory distress syndrome (ARDS), in which respiratory failure often occurs as a result of disruption of the alveolar—capillary membrane, which causes accumulation of proteinaceous pulmonary edema fluid and lack of oxygen uptake ability [76]. In this condition there has been some speculation that circulating EPC may be capable of restoring injured lung endothelium. For example, it is known that significant chimerism (37-42%) of pulmonary endothelial cells occurs in female recipients of male bone marrow transplants [77]. Furthermore, in patients with pneumonia infection there is a correlation between infection and circulating EPC, with higher numbers of EPC being indicative of reduced fibrosis [78]. The possibility that EPC are mobilized during ARDS and may be associated with benefit was examined in a study of 45 patients with acute lung injury in which a correlation between patients having higher number of cells capable of forming endothelial colonies in vitro and survival was made. Specifically, the patients with a colony count of >or =35 had a mortality of approximately 30%, compared to patients with less than 35 colonies, which had a mortality of 61%. The correlation was significant after multivariable analysis correcting for age, sex, and severity of illness [79]. From an interventional perspective, transplantation of EPC into a rabbit model of acute lung injury resulted in reduction of leukocytic infiltrates and preservation of pulmonary cellular integrity [80].

Sepsis is a major cause of ARDS and is associated with acute systemic inflammation and vascular damage. Septic patients have elevated levels of injury associated signals and EPC mobilizers such as HMGB1 [81], SDF-1 [82], and VEGF [83]. Significant pathology of sepsis is associated with vascular leak and disseminated intravascular coagulation [84]. The importance of the vasculature in sepsis can perhaps be supported by the finding that the only drug to have an impact on survival, Activated Protein C, acts primarily through endothelial protection [85]. Septic patients are known to have increased circulating EPC as compared to controls. Becchi et al observed a correlation between VEGF and SDF-1 levels with a 4-fold rise in circulating EPC in septic patients as compared to healthy controls [82]. A correlation between EPC levels and survival after sepsis was reported in a study of 32 septic patients, 15 ICU patients, and 15 controls. Of the 8 patients who succumbed to sepsis by 28 days, as compared to 24 survivors, a significantly reduced EPC number in non-survivors was reported [86].

It appears that in conditions of acute injury, elevation of EPC in circulation occurs. Although studies in stroke [70-72], ARDS [79], and sepsis [86] seem to correlate outcome with extend of mobilization, work remains to be performed in assessing whether it is the EPC component that is responsible for benefits or other confounding variables. Taking into account the possibility that EPC may act as an endogenous repair mechanism, we will discuss data in chronic degenerative conditions in which circulating EPC appear to be suppressed.

Accordingly, in one embodiment, the invention teaches the use of the composition of ellagic acid, vitamin D3, beta 1,3 glucan and a ferment of the bacterium, *Lactobacillus fermentum*, with an extract of green tea, extract of goji berries, and extract of the root of *astragalus* added prior to fermentation, as a means of enhancing regenerative responses to injury.

There is need for angiogenesis and tissue remodeling in the context of various chronic inflammatory conditions. However in many situations it is the aberrant reparative processes that actually contribute to the pathology of disease. Examples of this include: the process of neointimal hyperplasia and subsequent plaque formation in response to injury to the vascular wall [87], the process of hepatic fibrosis as opposed to functional regeneration [88], or the post-infarct pathological remodeling of the myocardium which results in progressive heart failure [89]. In all of these situations it appears that not only the lack of regenerative cells, but also the lack of EPC is present. Conceptually, the need for reparative cells to heal the ongoing damage may have been so overwhelming that it leads to exhaustion of EPC numbers and eventual reduction in protective effect. Supporting this concept are observations of lower number of circulating EPC in inflammatory diseases, which may be the result of exhaustion. Additionally, the reduced telomeric length of EPC in patients with coronary artery disease [90], as well as reduction of telomere length in the EPC precursors that are found in the bone marrow [91, 92] suggests that exhaustion in response to long-term demand may be occurring. If the reparatory demands of the injury indeed lead to depletion of EPC progenitors, then administration of progenitors should have therapeutic effects.

Several experiments have shown that administration of EPC have beneficial effects in the disease process. For example, EPC administration has been shown to: decrease balloon injury induced neointimal hyperplasia [93], b) suppress carbon tetrachloride induced hepatic fibrosis [94, 95], and inhibit post cardiac infarct remodeling [96]. One caveat of these studies is that definition of EPC was variable, or in some cases a confounding effect of coadministered cells with regenerative potential may be present. However, overall, there does appear to be an indication that EPC play a beneficial role in supporting tissue regeneration. As discussed below, many degenerative conditions, including healthy aging, are associated with a low-grade inflammation. There appears to be a causative link between this inflammation and reduction in EPC function.

Inflammatory conditions present with features, which although not the rule, appear to have commonalities. For example, increases in inflammatory markers such as C-reactive protein (CRP), erythrocyte sedimentation rate, and cytokines such as TNF-alpha and IL-18 have been described in diverse conditions ranging from organ degenerative conditions such as heart failure [97, 98], kidney failure [99, 100], and liver failure [101, 102] to autoimmune conditions such as rheumatoid arthritis [103] and Crohn's Disease [104], to healthy aging [105, 106]. Other markers of inflammation include products of immune cells such as neopterin, a metabolite that increases systemically with healthy aging [107], and its concentration positively correlates with cognitive deterioration in various age-related conditions such as Alzheimer's [108]. Neopterin is largely secreted by macrophages, which also produce inflammatory mediators such as TNF-alpha, IL-1, and IL-6, all of which are associated with chronic inflammation of aging [109]. Interestingly, these cytokines are known to upregulate CRP, which also is associated with aging [110]. While there is no direct evidence that inflammatory markers actively cause shorted lifespan in humans, strong indirect evidence of their detrimental activities exists. For example, direct injection of recombinant CRP in healthy volunteers induces atherothrombotic endothelial changes, similar to those observed in aging [111]. In vitro administration of CRP to endothelial cells decreases responsiveness to vasoactive factors, resembling the human age-associated condition of endothelial hyporesponsiveness [112].

Another important inflammatory mediator found elevated in numerous degenerative conditions is the cytokine TNF-alpha. Made by numerous cells, but primarily macrophages, TNF-alpha is known to inhibit proliferation of repair cells in the body, such as oligodendrocytes in the brain [113], and suppress activity of endogenous stem cell pools [114, 115]. TNF-alpha decreases EPC viability, an effect that can be overcome, at least in part by antioxidant treatment [116]. Administration of TNF-alpha blocking agents has been demonstrated to restore both circulating EPC, as well as endothelial function in patients with inflammatory diseases such as rheumatoid arthritis [36, 117, 118].

It appears that numerous degenerative conditions are associated with production of inflammatory mediators, which directly suppress EPC production or activity. This may be one of the reasons for findings of reduced EPC and FMD indices in patients with diverse inflammatory conditions. In addition to the direct effects, the increased demand for de novo EPC production in inflammatory conditions would theoretically lead to exhaustion of EPC precursors cells by virtue of telomere shortening.

Accordingly, in one embodiment, the invention teaches the use of the composition of ellagic acid, vitamin D3, beta 1,3 glucan and a ferment of the bacterium, *Lactobacillus fermentum*, with an extract of green tea, extract of goji berries, and extract of the root of *astragalus* added prior to fermentation, as a means of derepressing circulating EPC in conditions of chronic inflammation.

On average somatic cells can divide approximately 50 times, after which they undergo senescence, die or become cancerous. This limited proliferative ability is dependent on the telomere shortening problem. Every time cells divide the ends of the chromosomes called "telomeres" (complexes of tandem TTAGGGG repeats of DNA and proteins), are not completely replicated, thus they progressively get shorter [119]. Once telomeres reach a critical limit p53, p21, and p16 pathways are activated as a DNA damage response reaction instructing the cell to exit cell cycling. Associated with the process of senescence, the cells start expressing inflammatory cytokines such as IL-1 [120, 121], upregulation of adhesion molecules that attract inflammatory cells such as monocytes [122, 123], and morphologically take a flattened, elongated appearance. Physiologically, the process of cellular senescence caused in response to telomere shortening is believed to be a type of protective mechanism that cells have to prevented carcinogenesis [124]. At a whole organism level the association between telomere length and age has been made [125], as well, disorders of premature aging such as ataxia telangiectasia are characterized by accelerated telomere shortening [126].

The importance of this limited proliferative ability becomes apparent in our discussion of EPC. In general there is a need for continual endothelial cell replacement from EPC. Because the endothelial cells are exposed to enormous continual sheer stress of blood flow, mechanisms of repair and proliferation after injury need to exist. Theoretically, the more sheer stress on a particular artery, the more cell division would be required to compensate for cell loss. Indeed this appears to be the case. For example, telomeres are shorter in arteries associated with higher blood flow and sheer stress (like the iliac artery) as compared to arteries of lower stress such as the mammary artery [127]. The theory that senescence may be associated with atherosclerosis is supported since the iliac artery, which is associated with higher proliferation of endothelial cells and is also at a higher risk of atherosclerosis, thus prompting some investigators to propose atherosclerosis being associated with endothelial senescence [128, 129].

In an interesting intervention study Satoh et al examined 100 patients with coronary artery disease and 25 control patients. Telomere lengths were reduced in EPC of coronary artery disease patients as compared to controls. Lipid lowering therapy using agents such as atorvastatin has previously been shown to reduced oxidative stress and increase circulating EPC. Therapy with lipid lowering agents in this study resulted in preservation of telomeric length, presumably by decreasing the amount of de novo EPC produced, as well as oxidative stress leading to telomere erosion [130]. One important consideration when discussing telomere shortening of EPC is the difference between replicative senescence, which results from high need for differentiated endothelial cells, and stress induced senescence, in which inflammatory mediators can directly lead to telomere shortening. For example, smoking associated oxidative stress has been linked to stress induced senescence in clinical studies [131], whereas other studies have implicated inflammatory agents such as interferon gamma [132], TNF-alpha [133], and oxidative mediators as inducers of stress induced senescence [134].

Accordingly, in one embodiment, the invention teaches the use of the composition of ellagic acid, vitamin D3, beta 1,3 glucan and a ferment of the bacterium, *Lactobacillus fermentum*, with an extract of green tea, extract of goji berries, and extract of the root of *astragalus* added prior to fermentation, as a means of preventing exhaustion of circulating EPC.

EXAMPLES

1. Quantitative Analysis of CD133-positive and CD34-positive Cells after Stem-Kine Administration Peripheral blood mononuclear cells were isolated by Ficoll-Hypaque. Cells were stained by CD133, CD34 and CD45 antibodies and the level of markers' expression was measured according to the procedure described in methods. Flow-cytometric analysis of the samples for different periods before and during supplementation demonstrated that number of CD133-positive and CD34-positive cells in circulation was increased during supplementation. Data of the percentage of $CD133^+$ and $CD34^+$ cells selected from $PE^{bright}/FITC^{dim/negative}$ cells of peripheral blood mononuclear cell population at different time before and during intervention are presented in Table 1. Results shown in table are averaged values for all subjects of the percentage of CD133 and CD34 positive cells, the average values of these percentages normalized on the level of CD133 or CD34 positive cells before supplementation and calculated percentage of stem cell mobilization. The average percentage (mean±SD) of CD133+/CD45− cells was 0.012±0.008 before supplementation and 0.02±0.01 after two days and seven days of supplementation. We found that for the most of the subjects, mobilization of CD133 cells in circulation during Stem-Kine supplementation reached peak value between 48 hours and 7 days of supplementation. Eight subjects had peak of mobilized stem cells on the 2nd day, for seven subjects the maximum amount of CD133-posirtive cells was measured on $7^{th}$ day, and three subjects demonstrated maximum percentage of CD133 mobilization on $14^{th}$ day. Difference of the level of CD133 cells in circulation was statistically significant for two and seven days of Stem-Kine supplementation (p<0.02).

TABLE I

| | Average values of CD133-positive cells, ratios of pre to post measurements and percentage of stem/progenitor cell mobilization | | | | | Average values of CD34-positive cells, ratios of pre to post measurements and percentage of stem/progenitor cell mobilization | | | | |
|---|---|---|---|---|---|---|---|---|---|---|
| date | Conc. % | SE | Average ratio | SE | % of mobilization | Conc. % | SE | Average ratio | SE | % of mobilization |
| 0 | 0.012 | 0.002 | 1.00 | | | 0.062 | 0.007 | 1.00 | | |
| 1 | 0.014 | 0.002 | 1.38 | 0.19 | 37.6 | 0.069 | 0.007 | 1.20 | 0.12 | 19.8 |
| 2 | 0.020 | 0.003 | 1.99 | 0.42 | 98.8 | 0.071 | 0.009 | 1.17 | 0.13 | 17.3 |
| 7 | 0.020 | 0.002 | 1.97 | 0.24 | 96.6 | 0.072 | 0.008 | 1.25 | 0.15 | 25.0 |
| 14 | 0.012 | 0.001 | 1.33 | 0.21 | 32.6 | 0.077 | 0.009 | 1.29 | 0.16 | 28.5 |

Figure 2:
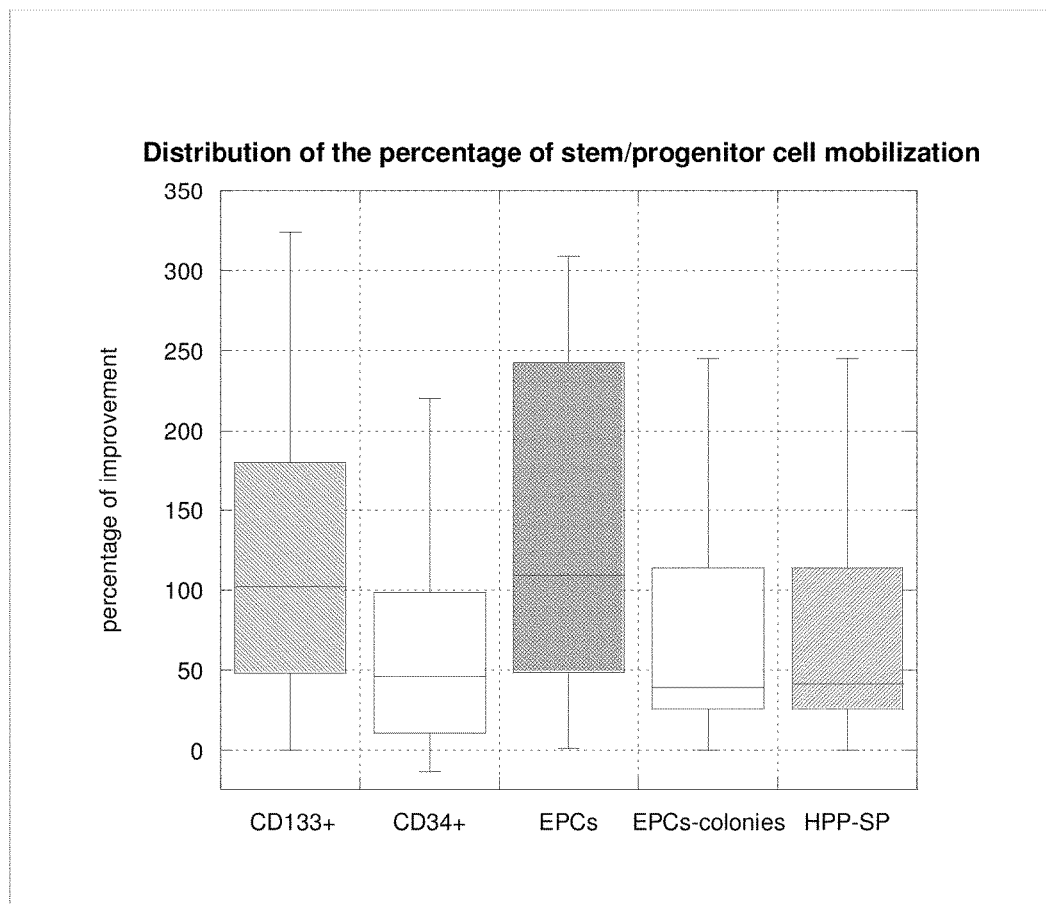
FIG. 2 is a graph depicting the distribution of the percentage of stem/progenitor cell mobilization.

As the number of stem cells in circulation depends on age and state of health, to exclude these factors and to find effect of supplement on stem cell mobilization, we normalized values measured during supplementation on values measured before supplementation. Mobilization of CD133-positive cells in circulation for different periods of time during supplementation was averaged for 18 subjects studied and the cumulative amount of CD133+ stem cells (average ratio of the percentage of CD133-positive cells in circulation before and during supplementation) is shown in FIG. 1. Measurements of the percentage of CD133-positive and CD34− positive cells in PBMCs indicated heterogeneity in the level of mobilized stem cells among different subjects. Distributions of the maximum values of stem cell mobilization for different subjects are shown in FIG. 2. Data presented in FIG. 2 show that interquartile range for CD133 mobilization was 50%-180% with the average maximum level of CD133-positive cell mobilization equals 120%.

Average percentage of CD34-positive cells for all subjects was 0.062%±0.029% (range 0.015%-0.1%) before supplementation and the maximum average percentage was 0.077%±0.037% (range 0.019%-0.145%) during supplementation. The distribution of the level of improvement of CD34-positive cells in circulation (percentage of maximum mobilization) is shown in FIG. 2. The individual values of response differed for different subjects and the maximum percentage of CD34 mobilized cells was 60% with interquartile range 10%-98%. Difference between average percentages of CD34+ cells in circulation was not significant for first days of supplementation and one-sided p-value was 0.05 for 7 days and 14 days of supplementation.

2. Characterization of the Mobilization of Endothelial Progenitor Cells in Circulation by Stem-Kine supplement One of the methods used in our study to characterize endothelial progenitor cells was immunofluorescent staining and measurements of endothelial progenitor markers by flow cytometry. Phenotype characterization of EPCs was confirmed by the expression of endothelial cell marker KDR and stem cell marker CD34. Cells positive for both markers were counted as endothelial progenitor cells. The level of EPCs was measured for each person at five different time points, normalized on the level of EPCs before supplementation and used for calculations of the level of mobilization of these cells in circulation. The number of EPCs in circulation was changed during supplementation and Stem-Kine supplementation influenced the concentration of endothelial progenitor cells.

Figure 3:
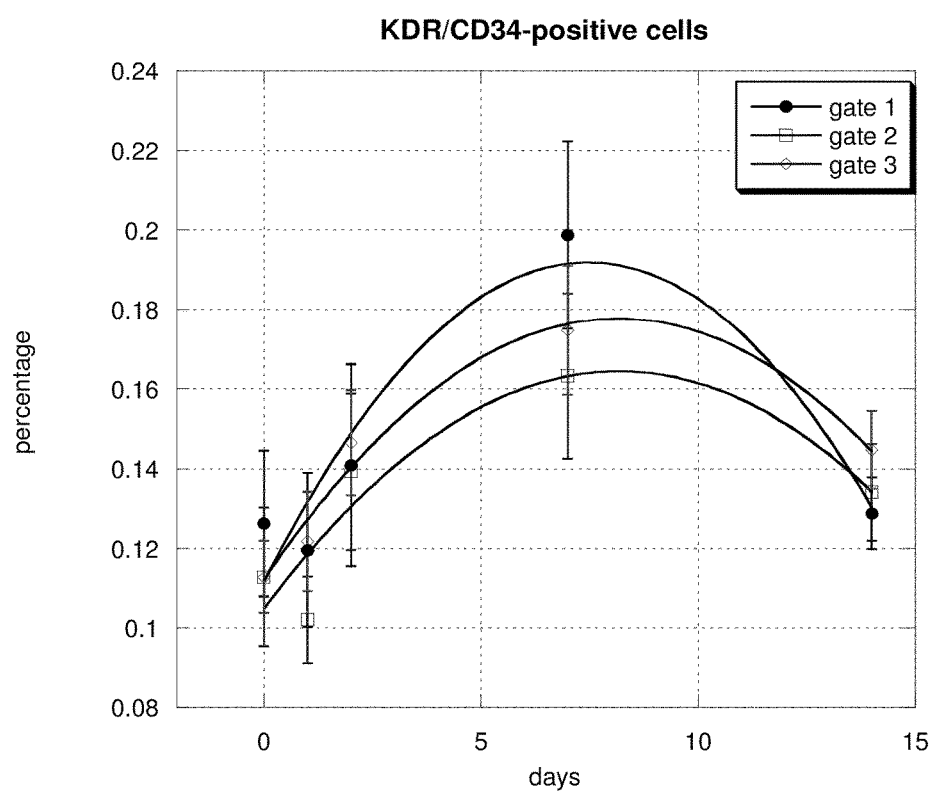
FIG. 3 is a graph showing the percentage of KDR/CD-34-positive over the course of days.
Figure 4:
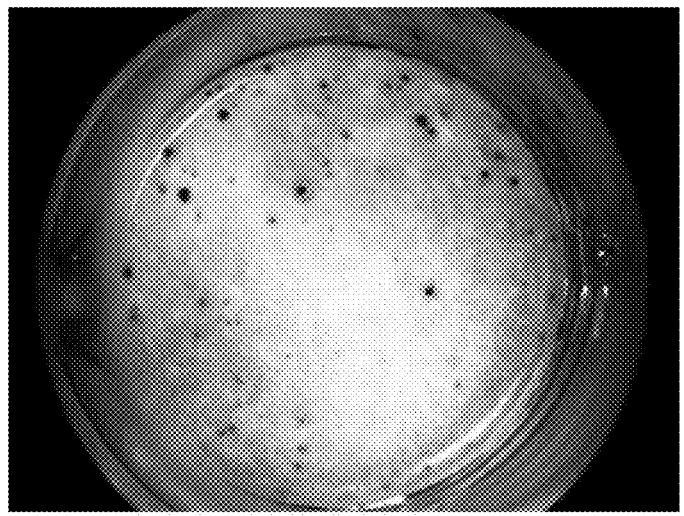
FIG. 4 is an image showing CHU-Hill colonies of EPCs stained by Giemsa stain.

The results of analysis demonstrated that number of endothelial progenitor cells was increased during Stem-Kine supplementation. Dependence of the average level of endothelial progenitor cells on time during supplementation for three different methods of EPCs' selection is shown in FIG. 3. The values of the average percentages of $KDR^+$/$CD34^+$ cells in circulation for different periods before and during supplementation, average ratio of percentage of EPCs before and during supplementation and average level of endothelial progenitor cell mobilization measured by several methods of positive cell selection are shown in Table 2.

concentration of serum, growth factors utilized (VEGF, IGF, FGF-b) and times in culture vary between researchers. Our chosen method of the growing colonies of endothelial progenitor cells is described in methods. Separated PBMCs were seeded in 24-well fibronectin-coated plates with concentration 1 M per wells for 5 days. After 5 days in culture, colonies were fixed by methanol and stained by Giemsa stain. The example of the images of the colonies is shown in FIG. 4.

Colonies were counted by AlphaEase software and by microscope. Analysis of the colonies from different subjects demonstrated that morphology of the colonies varied among different donors in term of size of colonies or the number of elongated sprouts at the periphery, but qualitative analysis was made only for number of colonies.

The broad range of variations between individuals was measured by colony growing assay. Number of colonies grown from 1M PBMCs ranged from 9 to 80 for different

TABLE II

| | Endothelial progenitor cells selected in gate "PE-bright/FITC-bright" cells | | | | | Endothelial progenitor cells selected in gate "PE-bright/SS-low" from FITC-bright population | | | | |
|---|---|---|---|---|---|---|---|---|---|---|
| date | average | SE | ratio | SE | % of mobilization | average | SE | ratio | SE | % of mobilization |
| 0 | 0.113 | 0.017 | 1.00 | | | 0.112 | 0.009 | 1.00 | 0.00 | |
| 1 | 0.102 | 0.011 | 1.27 | 0.18 | 27 | 0.122 | 0.012 | 1.04 | 0.06 | 4 |
| 2 | 0.139 | 0.020 | 1.50 | 0.14 | 50 | 0.147 | 0.013 | 1.36 | 0.12 | 35 |
| 7 | 0.163 | 0.021 | 1.99 | 0.18 | 99 | 0.175 | 0.016 | 1.74 | 0.21 | 74 |
| 14 | 0.134 | 0.012 | 1.78 | 0.27 | 78 | 0.145 | 0.010 | 1.39 | 0.12 | 39 |

Percentage of KDR+/CD34+ cells averaged for all subjects was increased from 0.12%±0.02% before supplementation to the maximum level (0.16%-0.2%)±0.02% on the seventh day of supplementation. Example of the distribution of the maximum percentage of EPCs' mobilization by Stem-Kine supplementation for all subjects and for one method of cell selection is shown in FIG. 2. The level of mobilization of EPCs in circulation differed for different subjects with interquartile distance 50%-240% and average value 140% for one method of EPCs' selection and interquartile distance 80%-260% with average value 220% for second method of EPCs selections. Difference of the level of EPCs in circulation was statistically significant for two and seven days of Stem-Kine supplementation (p<0.02). Practically in all subjects, the maximum of the endothelial cell mobilization was measured on 7th day of supplementation (except for three subjects with maximum values on $14^{th}$ days and one subject with maximum value on $2^{nd}$ day).

3. Quantitation of Endothelial Progenitor Cells by CFU-Hill Assay

The stimulatory effect of Stem-Kine on endothelial progenitor cells was conformed by colony formation assay. We performed second test to measure EPCs, as many of the markers that distinguish endothelial progenitor cells are found on other cells populations (hematopoietic cells and differentiated endothelial cells). Therefore, we decided to support our flow-cytometry data by measuring colonies formed by EPCs (CFU-Hill assay).

Figure 5:
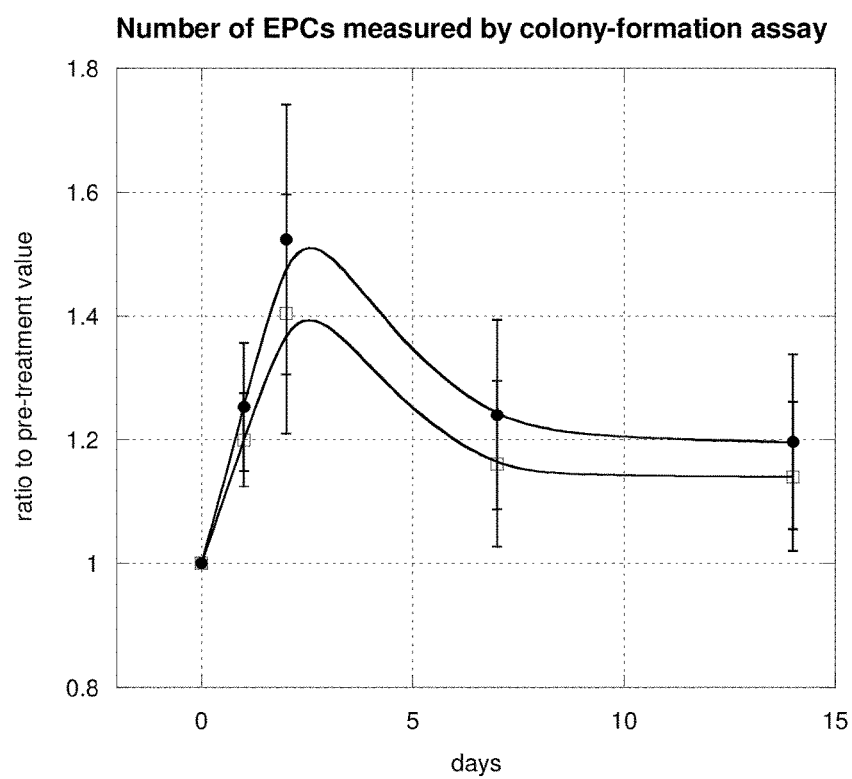
FIG. 5 is a graph depicting the number of EPCs measured by colony-formation assay over days.

There are no standard procedure for the isolation and in vitro culture of EPCs. Most commonly, mononuclear cells are cultured on plastic covered by fibronectin, type 1 collagen or gelatin with either adherent or non-adherent fraction considered to contain the EPCs. The medium formulation, subjects. To find dependence in developed colonies on supplementation, for each subject number of colonies for different time points during supplementation were normalized on number of colonies before treatment. Data presented in FIG. 5 represent the relative number of the measured colonies for different periods before and during supplementation (rhombs—number of colonies counted by microscope, squares—number of colonies measured by AlphaEase software).

In comparison with the pre-intervention level, there was increase in the levels of colony formation after 24 hrs and 48 hrs of supplementation (p<0.05). Distribution of the maximum percentage of EPC mobilization is shown in FIG. 1 (interquartile range 25%-114%, average maximum value 72%).

4. Analysis of the Number of the Progenitor Cells in Circulation by HALO Assay For the analysis of the level of progenitor cells in PBMCs, HALO assay was applied that is based on the classical colony-forming assay procedure. In our study, we used HALO-SC2 assay, in which stem cells and progenitor cells are stimulated with EPO, GM-CSF, G-CSF, IL-3, IL-6 and SCF. Cells were plated with and without addition of growth factors. The level of ATP was measured by bioluminescence assay in wells with stimulated and not stimulated cells after 5 days of exposure to growth factors. Average values of ATP in cells grown with added growth factors were normalized on the average level of ATP in cells in wells without growth factors.

We found that the level of cell proliferation measured by this assay is sensitive to the number of plated cells. For higher number of plated cells, coefficient of proliferation or the ratio of ATP in wells with stimulated and non-stimulated cells was decreased with the inverse coefficient of correlation R=0.7. As the variability in the plated cell number caused the variability in the results, cells were plated with the same concentration ~20000 cells per well for different periods of measurements.

Figures 6A, 6B:
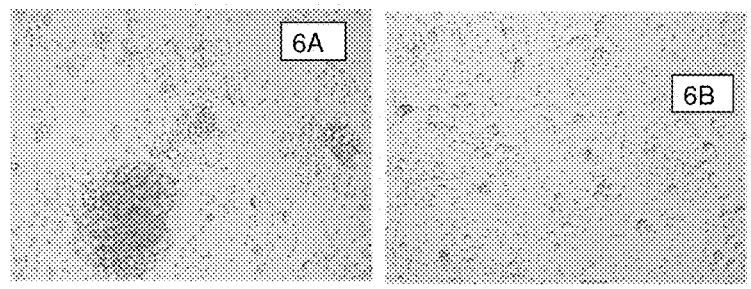
FIGS. 6A and 6B depict a comparison between cells grown in wells with growth factor (6A) and without growth factor (6B).

Addition of growth factors made possible cells to proliferate and differentiate in response to growth factors. This process is shown in FIG. 6 for cells grown for 5 days in medium with growth factors (a) and without growth factors (b).

Figure 7:
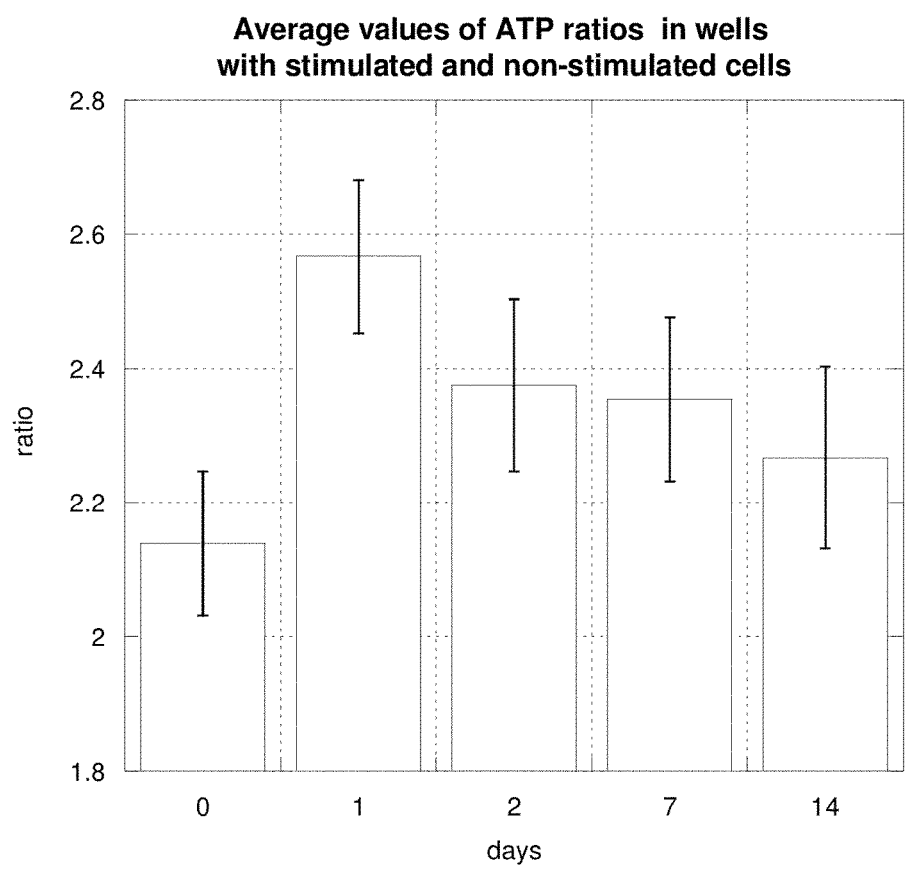
FIG. 7 is a graph depicting the average value of ATP ratios in wells with stimulated and non-stimulated cells.

The level of proliferation is defined by the presence of progenitor and stem cells in population of plated cells. During incubation, these cells are stimulated by growth factors to proliferate and divide. The higher number of stem cells and progenitor cells in PBMCs, the higher level of cell proliferation and higher level of ATP measured by bioluminescence assay in wells with growth factors. Base on this assumption, we considered that the ratio of ATP in wells with stimulated cells to ATP in wells with non-stimulated cells could characterize the population of stem and progenitor cells in cell population, and to measure the effect of Stem-Kine on the mobilization of stem and progenitor cells in blood. Data presented in FIG. 7 demonstrate the averaged for all subjects ratio (mean±SE) of ATP in wells with stimulated cells to ATP in wells with non-stimulated cells for different periods before and during supplementation with Stem-Kine.

Ratio of the average ATP was increased after 24 hrs of supplementation from pre-intervention level of 2.16±0.0.44 to 2.57±0.47. After 48 hrs and 7 days of supplementation, the ratio was decreased to 2.36±0.5 and 2.35±0.5. Statistical analysis showed significant difference of the mean ratio over pre-intervention level for 48 hrs (p<0.02). Distribution of the maximum values of cell proliferation is shown in FIG. 2 (interquartile range 25%-114%, average 73%).

Each of the references provided herein, including those listed below, are expressly incorporated by reference herein in their entireties.

REFERENCES

1. Park, H. C., et al., *Post-obstructive regeneration of the kidney is derailed, when surge in renal stem cells during the course of unilateral ureteral obstruction is halted.* Am J Physiol Renal Physiol, 2009.
2. Penn, M. S., *Importance of the SDF-1:CXCR4 axis in myocardial repair.* Circ Res, 2009. 104(10): p. 1133-5.
3. Wang, Y., Y. Deng, and G. Q. Zhou, *SDF-1alpha/CXCR4-mediated migration of systemically transplanted bone marrow stromal cells towards ischemic brain lesion in a rat model.* Brain Res, 2008. 1195: p. 104-12.
4. Allan, D. S., et al., *Mobilization of circulating vascular progenitors in cancer patients receiving external beam radiation in response to tissue injury.* Int J Radiat Oncol Biol Phys, 2009. 75(1): p. 220-4.
5. Tan, B. T., M. M. Lee, and R. Ruan, *Bone-marrow-derived cells that home to acoustic deafened cochlea preserved their hematopoietic identity.* J Comp Neurol, 2008. 509 (2): p. 167-79.
6. Kobbe, G., et al., *Pegfilgrastim for PBSC mobilization and autologous haematopoietic SCT.* Bone Marrow Transplant, 2009. 43(9): p. 669-77.
7. Subramaniyam, V., et al., *Bone marrow mobilization with granulocyte macrophage colony-stimulating factor improves endothelial dysfunction and exercise capacity in patients with peripheral arterial disease.* Am Heart J, 2009. 158(1): p. 53-60 e1.
8. Ballen, K. K., et al., *Phase I trial of parathyroid hormone to facilitate stem cell mobilization.* Biol Blood Marrow Transplant, 2007. 13(7): p. 838-43.
9. *Plerixafor: AMD 3100, AMD3100, JM 3100, SDZ SID 791.* Drugs R D, 2007. 8(2): p. 113-9.
10. Lombaert, I. M., et al., *Cytokine treatment improves parenchymal and vascular damage of salivary glands after irradiation.* Clin Cancer Res, 2008. 14(23): p. 7741-50.
11. Lombaert, I. M., et al., *Mobilization of bone marrow stem cells by granulocyte colony-stimulating factor ameliorates radiation-induced damage to salivary glands.* Clin Cancer Res, 2006. 12(6): p. 1804-12.
12. Brunner, S., et al., *G-CSF treatment after myocardial infarction: impact on bone marrow-derived vs cardiac progenitor cells.* Exp Hematol, 2008. 36(6): p. 695-702.
13. Hokari, M., et al., *Synergistic effects of granulocyte-colony stimulating factor on bone marrow stromal cell transplantation for mice cerebral infarct.* Cytokine, 2009. 46(2): p. 260-6.
14. Tarella, C., et al., *Consistent bone marrow-derived cell mobilization following repeated short courses of granulocyte-colony-stimulating factor in patients with amyotrophic lateral sclerosis: results from a multicenter prospective trial.* Cytotherapy, 2009.
15. Leone, A. M., et al., *Usefulness of granulocyte colony-stimulating factor in patients with a large anterior wall acute myocardial infarction to prevent left ventricular remodeling (the rigenera study).* Am J Cardiol, 2007. 100(3): p. 397-403.
16. Wang, Y., et al., *Effect of mobilization of bone marrow stem cells by granulocyte colony stimulating factor on clinical symptoms, left ventricular perfusion and function in patients with severe chronic ischemic heart disease.* Int J Cardiol, 2005. 100(3): p. 477-83.
17. Gaia, S., et al., *Feasibility and safety of G-CSF administration to induce bone marrow-derived cells mobilization in patients with end stage liver disease.* J Hepatol, 2006. 45(1): p. 13-9.
18. Jensen, G. S., et al., *Mobilization of human CD34+ CD133+ and CD34+ CD133(−) stem cells in vivo by consumption of an extract from Aphanizomenon flos-aquae-related to modulation of CXCR4 expression by an L-selectin ligand?* Cardiovasc Revasc Med, 2007. 8(3): p. 189-202.
19. Herrmann, J. and A. Lerman, *The Endothelium—the Cardiovascular Health Barometer.* Herz, 2008. 33(5): p. 343-353.
20. Hamel, E., *Perivascular nerves and the regulation of cerebrovascular tone.* J Appl Physiol, 2006. 100(3): p. 1059-64.
21. Saenz de Tejada, I., et al., *Pathophysiology of erectile dysfunction.* J Sex Med, 2005. 2(1): p. 26-39.
22. Provis, J. M., et al., *Anatomy and development of the macula: specialisation and the vulnerability to macular degeneration.* Clin Exp Optom, 2005. 88(5): p. 269-81.
23. Izikki, M., et al., *Role for dysregulated endothelium-derived FGF2 signaling in progression of pulmonary hypertension.* Rev Mal Respir, 2008. 25(9): p. 1192.
24. Pautler, E. L., *The possible role and treatment of deficient microcirculation regulation in age-associated memory impairment.* Med Hypotheses, 1994. 42(6): p. 363-6.
25. McCarron, R. M., et al., *Endothelial-mediated regulation of cerebral microcirculation.* J Physiol Pharmacol, 2006. 57 Suppl 11: p. 133-44.

26. Nowak, J. Z., *Age-related macular degeneration (AMD): pathogenesis and therapy*. Pharmacol Rep, 2006. 58(3): p. 353-63.
27. Chai, S. J., E. Barrett-Connor, and A. Gamst, *Small-vessel lower extremity arterial disease and erectile dysfunction: The Rancho Bernardo study*. Atherosclerosis, 2009. 203(2): p. 620-5.
28. Tuder, R. M. and J. H. Yun, *Vascular endothelial growth factor of the lung: friend or foe*. Curr Opin Pharmacol, 2008. 8(3): p. 255-60.
29. Kelm, M., *Flow-mediated dilatation in human circulation: diagnostic and therapeutic aspects*. Am J Physiol Heart Circ Physiol, 2002. 282(1): p. H1-5.
30. Celermajer, D. S., et al., *Non-invasive detection of endothelial dysfunction in children and adults at risk of atherosclerosis*. Lancet, 1992. 340(8828): p. 1111-5.
31. Palmer, R. M., A. G. Ferrige, and S. Moncada, *Nitric oxide release accounts for the biological activity of endothelium-derived relaxing factor*. Nature, 1987. 327 (6122): p. 524-6.
32. Ahlers, B. A., et al., *An age-related decline in endothelial function is not associated with alterations in L-arginine transport in humans*. J Hypertens, 2004. 22(2): p. 321-7.
33. Taddei, S., et al., *Aging and endothelial function in normotensive subjects and patients with essential hypertension*. Circulation, 1995. 91(7): p. 1981-7.
34. Andrawis, N., D. S. Jones, and D. R. Abernethy, *Aging is associated with endothelial dysfunction in the human forearm vasculature*. J Am Geriatr Soc, 2000. 48(2): p. 193-8.
35. Ghiadoni, L., et al., *Endothelial dysfunction and oxidative stress in chronic renal failure*. J Nephrol, 2004. 17(4): p. 512-9.
36. Bilsborough, W., et al., *Anti-tumour necrosis factor-alpha therapy over conventional therapy improves endothelial function in adults with rheumatoid arthritis*. Rheumatol Int, 2006. 26(12): p. 1125-31.
37. Roifman, I., et al., *Evidence of endothelial dysfunction in patients with inflammatory bowel disease*. Clin Gastroenterol Hepatol, 2009. 7(2): p. 175-82.
38. Hurks, R., et al., *Early endothelial dysfunction in young type 1 diabetics*. Eur J Vasc Endovasc Surg, 2009. 37(5): p. 611-5.
39. Crisby, M., et al., *Circulating levels of autoantibodies to oxidized low-density lipoprotein and C-reactive protein levels correlate with endothelial function in resistance arteries in men with coronary heart disease*. Heart Vessels, 2009. 24(2): p. 90-5.
40. Dede, D. S., et al., *Assessment of endothelial function in Alzheimer's disease: is Alzheimer's disease a vascular disease?* J Am Geriatr Soc, 2007. 55(10): p. 1613-7.
41. Chong, A. Y., et al., *Endothelial dysfunction and damage in congestive heart failure: relation of flow-mediated dilation to circulating endothelial cells, plasma indexes of endothelial damage, and brain natriuretic peptide*. Circulation, 2004. 110(13): p. 1794-8.
42. Poredos, P., *Endothelial dysfunction in the pathogenesis of atherosclerosis*. Int Angiol, 2002. 21(2): p. 109-16.
43. Listi, F., et al., *PECAM-1/CD31 in infarction and longevity*. Ann N Y Acad Sci, 2007. 1100: p. 132-9.
44. Ballard, V. L. and J. M. Edelberg, *Targets for regulating angiogenesis in the ageing endothelium*. Expert Opin Ther Targets, 2007. 11(11): p. 1385-99.
45. Lu, C., et al., *Effect of age on vascularization during fracture repair*. J Orthop Res, 2008. 26(10): p. 1384-9.
46. Rivard, A., et al., *Age-dependent defect in vascular endothelial growth factor expression is associated with reduced hypoxia-inducible factor 1 activity*. J Biol Chem, 2000. 275(38): p. 29643-7.
47. Basak, G. W., et al., *Human embryonic stem cells hemangioblast express HLA-antigens*. J Transl Med, 2009. 7: p. 27.
48. Stump, M. M., et al., *Endothelium Grown from Circulating Blood on Isolated Intravascular Dacron Hub*. Am J Pathol, 1963. 43: p. 361-7.
49. Asahara, T., et al., *Isolation of putative progenitor endothelial cells for angiogenesis*. Science, 1997. 275 (5302): p. 964-7.
50. Takahashi, T., et al., *Ischemia-and cytokine-induced mobilization of bone marrow-derived endothelial progenitor cells for neovascularization*. Nat Med, 1999. 5(4): p. 434-8.
51. Asahara, T., et al., *Bone marrow origin of endothelial progenitor cells responsible for postnatal vasculogenesis in physiological and pathological neovascularization*. Circ Res, 1999. 85(3): p. 221-8.
52. Peichev, M., et al., *Expression of VEGFR-2 and AC133 by circulating human CD34(+) cells identifies a population of functional endothelial precursors*. Blood, 2000. 95(3): p. 952-8.
53. Korbling, M., et al., *Recombinant human granulocyte-colony-stimulating factor-mobilized and apheresis-collected endothelial progenitor cells: a novel blood cell component for therapeutic vasculogenesis*. Transfusion, 2006. 46(10): p. 1795-802.
54. Timmermans, F., et al., *Endothelial outgrowth cells are not derived from CD133+ cells or CD45+ hematopoietic precursors*. Arterioscler Thromb Vasc Biol, 2007. 27(7): p. 1572-9.
55. Rehman, J., et al., *Peripheral blood "endothelial progenitor cells" are derived from monocyte/macrophages and secrete angiogenic growth factors*. Circulation, 2003. 107(8): p. 1164-9.
56. Rohde, E., et al., *Blood monocytes mimic endothelial progenitor cells*. Stem Cells, 2006. 24(2): p. 357-67.
57. Foteinos, G., et al., *Rapid endothelial turnover in atherosclerosis prone areas coincides with stem cell repair in apolipoprotein E-deficient mice*. Circulation, 2008. 117(14): p. 1856-63.
58. Werner, N., et al., *Intravenous transfusion of endothelial progenitor cells reduces neointima formation after vascular injury*. Circ Res, 2003. 93(2): p. e17-24.
59. Wassmann, S., et al., *Improvement of endothelial function by systemic transfusion of vascular progenitor cells*. Circ Res, 2006. 99(8): p. e74-83.
60. Edelberg, J. M., et al., *Young adult bone marrow-derived endothelial precursor cells restore aging-impaired cardiac angiogenic function*. Circ Res, 2002. 90(10): p. E89-93.
61. Ceradini, D. J. and G. C. Gurtner, *Homing to hypoxia: HIF-1 as a mediator of progenitor cell recruitment to injured tissue*. Trends Cardiovasc Med, 2005. 15(2): p. 57-63.
62. Schomig, K., et al., *Interleukin-8 is associated with circulating CD133+ progenitor cells in acute myocardial infarction*. Eur Heart J, 2006. 27(9): p. 1032-7.
63. Shintani, S., et al., *Mobilization of endothelial progenitor cells in patients with acute myocardial infarction*. Circulation, 2001. 103(23): p. 2776-9.
64. Andrassy, M., et al., *High-mobility group box-1 in ischemia-reperfusion injury of the heart*. Circulation, 2008. 117(25): p. 3216-26.

65. Palumbo, R., et al., *Cells migrating to sites of tissue damage in response to the danger signal HMGB1 require NF-kappaB activation.* J Cell Biol, 2007. 179(1): p. 33-40.

66. Gill, M., et al., *Vascular trauma induces rapid but transient mobilization of VEGFR2(+)AC133(+) endothelial precursor cells.* Circ Res, 2001. 88(2): p. 167-74.

67. Wojakowski, W., et al., *Mobilization of CD34/CXCR4+, CD34/CD117+, c-met+ stem cells, and mononuclear cells expressing early cardiac, muscle, and endothelial markers into peripheral blood in patients with acute myocardial infarction.* Circulation, 2004. 110(20): p. 3213-20.

68. Massa, M., et al., *Increased circulating hematopoietic and endothelial progenitor cells in the early phase of acute myocardial infarction.* Blood, 2005. 105(1): p. 199-206.

69. Chang, L. T., et al., *Role of stromal cell-derived factor-1 alpha, level and value of circulating interleukin-10 and endothelial progenitor cells in patients with acute myocardial infarction undergoing primary coronary angioplasty.* Circ J, 2009. 73(6): p. 1097-104.

70. Sobrino, T., et al., *The increase of circulating endothelial progenitor cells after acute ischemic stroke is associated with good outcome.* Stroke, 2007. 38(10): p. 2759-64.

71. Dunac, A., et al., *Neurological and functional recovery in human stroke are associated with peripheral blood CD34+ cell mobilization.* J Neurol, 2007. 254(3): p. 327-32.

72. Yip, H. K., et al., *Level and value of circulating endothelial progenitor cells in patients after acute ischemic stroke.* Stroke, 2008. 39(1): p. 69-74.

73. Wu, J., et al., *Intravenously administered bone marrow cells migrate to damaged brain tissue and improve neural function in ischemic rats.* Cell Transplant, 2008. 16(10): p. 993-1005.

74. Chen, Z. Z., et al., *Beneficial effect of autologous transplantation of bone marrow stromal cells and endothelial progenitor cells on cerebral ischemia in rabbits.* Neurosci Lett, 2008. 445(1): p. 36-41.

75. Deng, Y. B., et al., *Intravenously administered BMSCs reduce neuronal apoptosis and promote neuronal proliferation through the release of VEGF after stroke in rats.* Neurol Res, 2009.

76. Ware, L. B. and M. A. Matthay, *The acute respiratory distress syndrome.* N Engl J Med, 2000. 342(18): p. 1334-49.

77. Suratt, B. T., et al., *Human pulmonary chimerism after hematopoietic stem cell transplantation.* Am J Respir Crit. Care Med, 2003. 168(3): p. 318-22.

78. Yamada, M., et al., *Increased circulating endothelial progenitor cells in patients with bacterial pneumonia: evidence that bone marrow derived cells contribute to lung repair.* Thorax, 2005. 60(5): p. 410-3.

79. Burnham, E. L., et al., *Increased circulating endothelial progenitor cells are associated with survival in acute lung injury.* Am J Respir Crit. Care Med, 2005. 172(7): p. 854-60.

80. Lam, C. F., et al., *Autologous transplantation of endothelial progenitor cells attenuates acute lung injury in rabbits.* Anesthesiology, 2008. 108(3): p. 392-401.

81. Hatada, T., et al., *Plasma concentrations and importance of High Mobility Group Box protein in the prognosis of organ failure in patients with disseminated intravascular coagulation.* Thromb Haemost, 2005. 94(5): p. 975-9.

82. Becchi, C., et al., *The increase of endothelial progenitor cells in the peripheral blood: a new parameter for detecting onset and severity of sepsis.* Int J Immunopathol Pharmacol, 2008. 21(3): p. 697-705.

83. Liu, Y., S. D. Song, and H. X. Wang, *[A clinical study of the serum vascular endothelial growth factor in patients with severe sepsis].* Zhongguo Wei Zhong Bing Ji Jiu Yi Xue, 2009. 21(3): p. 172-4.

84. Matsuda, N. and Y. Hattori, *Vascular biology in sepsis: pathophysiological and therapeutic significance of vascular dysfunction.* J Smooth Muscle Res, 2007. 43(4): p. 117-37.

85. Regnault, V. and B. Levy, *Recombinant activated protein C in sepsis: endothelium protection or endothelium therapy?* Crit. Care, 2007. 11(1): p. 103.

86. Rafat, N., et al., *Increased circulating endothelial progenitor cells in septic patients: correlation with survival.* Crit. Care Med, 2007. 35(7): p. 1677-84.

87. Hristov, M., et al., *Adult progenitor cells in vascular remodeling during atherosclerosis.* Biol Chem, 2008. 389(7): p. 837-44.

88. Zhao, Q., et al., *Stem/progenitor cells in liver injury repair and regeneration.* Biol Cell, 2009. 101(10): p. 557-71.

89. Sun, Y., *Myocardial repair/remodelling following infarction: roles of local factors.* Cardiovasc Res, 2009. 81(3): p. 482-90.

90. Ogami, M., et al., *Telomere shortening in human coronary artery diseases.* Arterioscler Thromb Vasc Biol, 2004. 24(3): p. 546-50.

91. Goldschmidt-Clermont, P. J., *Loss of bone marrow-derived vascular progenitor cells leads to inflammation and atherosclerosis.* Am Heart J, 2003. 146(4 Suppl): p. S5-12.

92. Spyridopoulos, I., et al., *Telomere gap between granulocytes and lymphocytes is a determinant for hematopoietic progenitor cell impairment in patients with previous myocardial infarction.* Arterioscler Thromb Vasc Biol, 2008. 28(5): p. 968-74.

93. Griese, D. P., et al., *Isolation and transplantation of autologous circulating endothelial cells into denuded vessels and prosthetic grafts: implications for cell-based vascular therapy.* Circulation, 2003. 108(21): p. 2710-5.

94. Liu, F., et al., *Transplanted endothelial progenitor cells ameliorate carbon tetrachloride-induced liver cirrhosis in rats.* Liver Transpl, 2009. 15(9): p. 1092-100.

95. Nakamura, T., et al., *Significance and therapeutic potential of endothelial progenitor cell transplantation in a cirrhotic liver rat model.* Gastroenterology, 2007. 133(1): p. 91-107 e1.

96. Xin, Z., et al., *Different biological properties of circulating and bone marrow endothelial progenitor cells in acute myocardial infarction rats.* Thorac Cardiovasc Surg, 2008. 56(8): p. 441-8.

97. Vila, V., et al., *Inflammation, endothelial dysfunction and angiogenesis markers in chronic heart failure patients.* Int J Cardiol, 2008. 130(2): p. 276-7.

98. von Haehling, S., et al., *Inflammatory biomarkers in heart failure revisited: much more than innocent bystanders.* Heart Fail Clin, 2009. 5(4): p. 549-60.

99. Stenvinkel, P., *Inflammation in end-stage renal disease—a fire that burns within.* Contrib Nephrol, 2005. 149: p. 185-99.

100. Porazko, T., et al., *IL-18 is involved in vascular injury in end-stage renal disease patients.* Nephrol Dial Transplant, 2009. 24(2): p. 589-96.

101. Nakae, H., et al., *Involvement of IL-18 and soluble fas in patients with postoperative hepatic failure.* Eur Surg Res, 2003. 35(2): p. 61-6.

102. Yumoto, E., et al., *Serum gamma-interferon-inducing factor (IL-18) and IL-10 levels in patients with acute hepatitis and fulminant hepatic failure.* J Gastroenterol Hepatol, 2002. 17(3): p. 285-94.

103. Petrovic-Rackov, L. and N. Pejnovic, *Clinical significance of IL-18, IL-15, IL-12 and TNF-alpha measurement in rheumatoid arthritis.* Clin Rheumatol, 2006. 25(4): p. 448-52.

104. Leach, S. T., et al., *Local and systemic interleukin-18 and interleukin-18-binding protein in children with inflammatory bowel disease.* Inflamm Bowel Dis, 2008. 14(1): p. 68-74.

105. Miles, E. A., et al., *Age-related increases in circulating inflammatory markers in men are independent of BMI, blood pressure and blood lipid concentrations.* Atherosclerosis, 2008. 196(1): p. 298-305.

106. Krabbe, K. S., M. Pedersen, and H. Bruunsgaard, *Inflammatory mediators in the elderly.* Exp Gerontol, 2004. 39(5): p. 687-99.

107. Svoboda, P., et al., *Neopterin, a marker of immune response, and 8-hydroxy-2'-deoxyguanosine, a marker of oxidative stress, correlate at high age as determined by automated simultaneous high-performance liquid chromatography analysis of human urine.* Anal Biochem, 2008. 383(2): p. 236-42.

108. Blasko, I., et al., *Cognitive deterioration in Alzheimer's disease is accompanied by increase of plasma neopterin.* J Psychiatr Res, 2007. 41(8): p. 694-701.

109. Capri, M., et al., *The genetics of human longevity.* Ann N Y Acad Sci, 2006. 1067: p. 252-63.

110. Ventura, E., et al., *Homocysteine and inflammation as main determinants of oxidative stress in the elderly.* Free Radic Biol Med, 2008.

111. van Leuven, S. I., et al., *ApoAI-phosphatidylcholine infusion neutralizes the atherothrombotic effects of C-reactive protein in humans.* J Thromb Haemost, 2008.

112. Nagaoka, T., et al., *C-reactive protein inhibits endothelium-dependent nitric oxide-mediated dilation of retinal arterioles via enhanced superoxide production.* Invest Ophthalmol V is Sci, 2008. 49(5): p. 2053-60.

113. Butovsky, O., et al., *Induction and blockage of oligodendrogenesis by differently activated microglia in an animal model of multiple sclerosis.* J Clin Invest, 2006. 116(4): p. 905-15.

114. Pickering, M. and J. J. O'Connor, *Pro-inflammatory cytokines and their effects in the dentate gyrus.* Prog Brain Res, 2007. 163: p. 339-54.

115. Pluchino, S., et al., *Persistent inflammation alters the function of the endogenous brain stem cell compartment.* Brain, 2008. 131(Pt 10): p. 2564-78.

116. Fiorito, C., et al., *Antioxidants increase number of progenitor endothelial cells through multiple gene expression pathways.* Free Radic Res, 2008. 42(8): p. 754-62.

117. Ablin, J. N., et al., *Effect of anti-TNFalpha treatment on circulating endothelial progenitor cells (EPCs) in rheumatoid arthritis.* Life Sci, 2006. 79(25): p. 2364-9.

118. Bosello, S., et al., *TNF-alpha blockade induces a reversible but transient effect on endothelial dysfunction in patients with long-standing severe rheumatoid arthritis.* Clin Rheumatol, 2008. 27(7): p. 833-9.

119. Harley, C. B., A. B. Futcher, and C. W. Greider, *Telomeres shorten during ageing of human fibroblasts.* Nature, 1990. 345(6274): p. 458-60.

120. Maier, J. A., et al., *Extension of the life-span of human endothelial cells by an interleukin-1 alpha antisense oligomer.* Science, 1990. 249(4976): p. 1570-4.

121. Schnabl, B., et al., *Replicative senescence of activated human hepatic stellate cells is accompanied by a pronounced inflammatory but less fibrogenic phenotype.* Hepatology, 2003. 37(3): p. 653-64.

122. Maier, J. A., M. Statuto, and G. Ragnotti, *Senescence stimulates U937-endothelial cell interactions.* Exp Cell Res, 1993. 208(1): p. 270-4.

123. Shelton, D. N., et al., *Microarray analysis of replicative senescence.* Curr Biol, 1999. 9(17): p. 939-45.

124. Parkinson, E. K., et al., *Replicative senescence as a barrier to human cancer.* Biochem Soc Trans, 2000. 28(2): p. 226-33.

125. Satoh, H., et al., *Telomere shortening in peripheral blood cells was related with aging but not with white blood cell count.* Jpn J Hum Genet, 1996. 41(4): p. 413-7.

126. Metcalfe, J. A., et al., *Accelerated telomere shortening in ataxia telangiectasia.* Nat Genet, 1996. 13(3): p. 350-3.

127. Chang, E. and C. B. Harley, *Telomere length and replicative aging in human vascular tissues.* Proc Natl Acad Sci USA, 1995. 92(24): p. 11190-4.

128. Caplan, B. A. and C. J. Schwartz, *Increased endothelial cell turnover in areas of in vivo Evans Blue uptake in the pig aorta.* Atherosclerosis, 1973. 17(3): p. 401-17.

129. Erusalimsky, J. D. and D. J. Kurz, *Cellular senescence in vivo: its relevance in ageing and cardiovascular disease.* Exp Gerontol, 2005. 40(8-9): p. 634-42.

130. Satoh, M., et al., *Effect of intensive lipid-lowering therapy on telomere erosion in endothelial progenitor cells obtained from patients with coronary artery disease.* Clin Sci (Lond), 2009. 116(11): p. 827-35.

131. Farhat, N., et al., *Stress-induced senescence predominates in endothelial cells isolated from atherosclerotic chronic smokers.* Can J Physiol Pharmacol, 2008. 86(11): p. 761-9.

132. Kim, K. S., et al., *Interferon-gamma induces cellular senescence through p53-dependent DNA damage signaling in human endothelial cells.* Mech Ageing Dev, 2009. 130(3): p. 179-88.

133. Mezzano, D., et al., *Inflammation, not hyperhomocysteinemia, is related to oxidative stress and hemostatic and endothelial dysfunction in uremia.* Kidney Int, 2001. 60(5): p. 1844-50.

134. Satoh, M., et al., *Association between oxidative DNA damage and telomere shortening in circulating endothelial progenitor cells obtained from metabolic syndrome patients with coronary artery disease.* Atherosclerosis, 2008. 198(2): p. 347-53.

135. Phillips, T., et al., *A dietary supplement attenuates IL-6 and CRP after eccentric exercise in untrained males.* Med Sci Sports Exerc, 2003. 35(12): p. 2032-7.

136. Regensteiner, J. G., et al., *Oral L-arginine and vitamins E and C improve endothelial function in women with type 2 diabetes.* Vasc Med, 2003. 8(3): p. 169-75.

137. Kalani, R., et al., *Effects of caloric restriction and exercise on age-related, chronic inflammation assessed by C-reactive protein and interleukin-6.* J Gerontol A Biol Sci Med Sci, 2006. 61(3): p. 211-7.

138. Colbert, L. H., et al., *Physical activity, exercise, and inflammatory markers in older adults: findings from the Health, Aging and Body Composition Study.* J Am Geriatr Soc, 2004. 52(7): p. 1098-104.

139. Thijssen, D. H., et al., *Vascular adaptations to 8-week cycling training in older men.* Acta Physiol (Oxf), 2007. 190(3): p. 221-8.

140. Abidov, M., et al., *Effect of Blueberin on fasting glucose, C-reactive protein and plasma aminotrans-* ferases, in female volunteers with diabetes type 2: double-blind, placebo controlled clinical study. Georgian Med News, 2006(141): p. 66-72.
141. Alexopoulos, N., et al., *The acute effect of green tea consumption on endothelial function in healthy individuals*. Eur J Cardiovasc Prev Rehabil, 2008. 15(3): p. 300-5.
142. Ridker, P. M., et al., *Rosuvastatin to prevent vascular events in men and women with elevated C-reactive protein*. N Engl J Med, 2008. 359(21): p. 2195-207.
143. Spiel, A. O., et al., *Simvastatin and rosuvastatin mobilize Endothelial Progenitor Cells but do not prevent their acute decrease during systemic inflammation*. Thromb Res, 2008. 123(1): p. 108-13.
144. Thum, T., et al., *Suppression of endothelial progenitor cells in human coronary artery disease by the endogenous nitric oxide synthase inhibitor asymmetric dimethylarginine*. J Am Coll Cardiol, 2005. 46(9): p. 1693-701.
145. Singh, S., et al., *Stem cells improve left ventricular function in acute myocardial infarction*. Clin Cardiol, 2009. 32(4): p. 176-80.
146. Martin-Rendon, E., et al., *Autologous bone marrow stem cells to treat acute myocardial infarction: a systematic review*. Eur Heart J, 2008. 29(15): p. 1807-18.
147. Abdel-Latif, A., et al., *Adult bone marrow-derived cells for cardiac repair: a systematic review and meta-analysis*. Arch Intern Med, 2007. 167(10): p. 989-97.
148. Rota, M., et al., *Bone marrow cells adopt the cardiomyogenic fate in vivo*. Proc Natl Acad Sci USA, 2007. 104(45): p. 17783-8.
149. Kajstura, J., et al., *Bone marrow cells differentiate in cardiac cell lineages after infarction independently of cell fusion*. Circ Res, 2005. 96(1): p. 127-37.
150. Psaltis, P. J., et al., *Concise review: mesenchymal stromal cells: potential for cardiovascular repair*. Stem Cells, 2008. 26(9): p. 2201-10.
151. Norol, F., et al., *GFP-transduced CD34+ and Lin-CD34- hematopoietic stem cells did not adopt a cardiac phenotype in a nonhuman primate model of myocardial infarct*. Exp Hematol, 2007. 35(4): p. 653-61.
152. Devanesan, A. J., et al., *Endothelial progenitor cells as a therapeutic option in peripheral arterial disease*. Eur J Vasc Endovasc Surg, 2009. 38(4): p. 475-81.
153. Jujo, K., M. Ii, and D. W. Losordo, *Endothelial progenitor cells in neovascularization of infarcted myocardium*. J Mol Cell Cardiol, 2008. 45(4): p. 530-44.
154. Jin, F., et al., *Degradation of BM SDF-1 by MMP-9: the role in G-CSF-induced hematopoietic stem/progenitor cell mobilization*. Bone Marrow Transplant, 2008. 42(9): p. 581-8.
155. Carion, A., et al., *Stromal-derived factor 1 and matrix metalloproteinase 9 levels in bone marrow and peripheral blood of patients mobilized by granulocyte colony-stimulating factor and chemotherapy. Relationship with mobilizing capacity of haematopoietic progenitor cells*. Br J Haematol, 2003. 122(6): p. 918-26.
156. Ratajczak, M. Z., et al., *A pivotal role of activation of complement cascade (CC) in mobilization of hematopoietic stem/progenitor cells (HSPC)*. Adv Exp Med Biol, 2008. 632: p. 47-60.
157. Lee, H. M., et al., *Impaired mobilization of hematopoietic stem/progenitor cells in CS-deficient mice supports the pivotal involvement of innate immunity in this process and reveals novel promobilization effects of granulocytes*. Leukemia, 2009.
158. Pitchford, S. C., et al., *Differential mobilization of subsets of progenitor cells from the bone marrow*. Cell Stem Cell, 2009. 4(1): p. 62-72.
159. Ince, H., et al., *Prevention of left ventricular remodeling with granulocyte colony-stimulating factor after acute myocardial infarction: final 1-year results of the Front-Integrated Revascularization and Stem Cell Liberation in Evolving Acute Myocardial Infarction by Granulocyte Colony-Stimulating Factor (FIRSTLINE-AMI) Trial*. Circulation, 2005. 112(9 Suppl): p. 173-80.
160. Zohlnhofer, D., et al., *Stem cell mobilization by granulocyte colony-stimulating factor in patients with acute myocardial infarction: a randomized controlled trial*. JAMA, 2006. 295(9): p. 1003-10.
161. Hill, J. M. and J. Bartunek, *The end of granulocyte colony-stimulating factor in acute myocardial infarction? Reaping the benefits beyond cytokine mobilization*. Circulation, 2006. 113(16): p. 1926-8.
162. Suzuki, K., et al., *Effect of granulocyte colony-stimulating factor treatment at a low dose but for a long duration in patients with coronary heart disease*. Circ J, 2006. 70(4): p. 430-7.
163. Napoli, R., et al., *Acute effects of growth hormone on vascular function in human subjects*. J Clin Endocrinol Metab, 2003. 88(6): p. 2817-20.
164. Napoli, R., et al., *Growth hormone corrects vascular dysfunction in patients with chronic heart failure*. J Am Coll Cardiol, 2002. 39(1): p. 90-5.
165. Devin, J. K., et al., *Low-dose growth hormone administration mobilizes endothelial progenitor cells in healthy adults*. Growth Horm IGF Res, 2008. 18(3): p. 253-63.
166. Thum, T., et al., *Age-dependent impairment of endothelial progenitor cells is corrected by growth-hormone-mediated increase of insulin-like growth-factor-1*. Circ Res, 2007. 100(3): p. 434-43.

The invention claimed is:
1. A method of treating a degenerative condition in a mammal through the steps of: a) identifying a deficiency in numbers and/or activity of circulating endothelial progenitor cells; b) administering a nutritional supplement capable of augmenting circulating levels of endothelial progenitor cells based on deficiency identified said nutritional supplement comprising ellagic acid, vitamin D3, beta 1,3 glucan and a ferment of the bacterium, *Lactobacillus fermentum,* with an extract of green tea, extract of goji berries, and extract of the root of *astragalus* added prior to fermentation; c) re-assessing circulating endothelial progenitor cell numbers; and d) further adjusting dose of said nutritional supplement based on response to supplementation.

* * * * *